United States Patent
Liebig et al.

(10) Patent No.: US 10,823,807 B2
(45) Date of Patent: Nov. 3, 2020

(54) METHOD FOR RECORDING MAGNETIC RESONANCE DATA, MAGNETIC RESONANCE FACILITY, COMPUTER PROGRAM AND ELECTRONICALLY READABLE DATA CARRIER

(71) Applicant: Siemens Healthcare GmbH, Erlangen (DE)

(72) Inventors: Patrick Liebig, Erlangen (DE); Robin Heidemann, Litzendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/779,980

(22) Filed: Feb. 3, 2020

(65) Prior Publication Data
US 2020/0249303 A1   Aug. 6, 2020

(30) Foreign Application Priority Data
Feb. 4, 2019 (DE) .................. 10 2019 201 385

(51) Int. Cl.
*G01R 33/561* (2006.01)
*G01R 33/58* (2006.01)
*G01R 33/44* (2006.01)

(52) U.S. Cl.
CPC ....... *G01R 33/5617* (2013.01); *G01R 33/446* (2013.01); *G01R 33/583* (2013.01)

(58) Field of Classification Search
CPC . G01R 33/5617; G01R 33/583; G01R 33/446
See application file for complete search history.

(56) References Cited

U.S. PATENT DOCUMENTS

| 5,742,163 A * | 4/1998 | Liu ................. G01R 33/56554 324/307 |
| 6,188,219 B1 * | 2/2001 | Reeder ................. G01R 33/58 324/307 |
| 6,697,507 B1 * | 2/2004 | Chapman ............. G01R 33/565 382/107 |
| 7,474,097 B2 * | 1/2009 | Bydder ................ G01R 33/561 324/307 |
| 7,643,863 B2 * | 1/2010 | Basser ............. G01R 33/56341 324/307 |
| 7,777,488 B2 * | 8/2010 | Gore .................. G01R 33/4824 324/307 |

(Continued)

OTHER PUBLICATIONS

Geraghty, Benjamin J. et al.: "Accelerated 3D Echo-Planar Imaging with Compressed Sensing for Time-Resolved Hyperpolarized 13C Studies"; in: Magnetic Resonance in Medicine; vol. 77; pp. 538-546; 2017; DOI: 10.1002/mrm.26125.

(Continued)

*Primary Examiner* — Dixomara Vargas
(74) *Attorney, Agent, or Firm* — Schiff Hardin LLP (57) ABSTRACT

Techniques are disclosed for recording magnetic resonance data with a magnetic resonance facility, wherein a three-dimensional echo-planar imaging sequence is used whereby following a single excitation period (e.g. "module") in an echo train, an echo count of k-space rows is read out in a read-out direction in the k-space, and interchanging takes place between these rows by means of gradient pulses of the two phase encoding directions.

11 Claims, 8 Drawing Sheets

(56) References Cited

U.S. PATENT DOCUMENTS

| | | | |
|---|---|---|---|
| 8,380,280 B2* | 2/2013 | Basser | G01R 33/56341 |
| | | | 324/309 |
| 9,581,671 B2* | 2/2017 | Dannels | G01R 33/56554 |
| 9,655,522 B2* | 5/2017 | Li | G06K 9/52 |
| 2005/0007100 A1* | 1/2005 | Basser | G01R 33/56341 |
| | | | 324/200 |
| 2007/0080685 A1* | 4/2007 | Bydder | G01R 33/561 |
| | | | 324/309 |
| 2010/0026294 A1 | 2/2010 | Lustig et al. | |
| 2014/0035582 A1* | 2/2014 | Boernert | G01R 33/5611 |
| | | | 324/312 |
| 2015/0073263 A1 | 3/2015 | Gdaniec et al. | |
| 2015/0097565 A1 | 4/2015 | Basha et al. | |
| 2015/0126850 A1* | 5/2015 | Cetingul | A61B 5/0402 |
| | | | 600/413 |
| 2015/0241537 A1* | 8/2015 | Dannels | G01R 33/56554 |
| | | | 324/309 |
| 2016/0104279 A1* | 4/2016 | Li | G06K 9/52 |
| | | | 382/131 |
| 2017/0199258 A1 | 7/2017 | Beck et al. | |

OTHER PUBLICATIONS

German Action dated Dec. 13, 2019, for Application No. 10 2019 201 385.6.

Hu, Simon, et al. 3D compressed sensing for highly accelerated hyperpolarized 13C MRSI with in vivo applications to transgenic mouse models of cancer, Magnetic Resonance in Medicine: An Official Journal of the International Society for Magnetic Resonance in Medicine, 2010, pp. 312-321.

Larson, Peder EZ, et al. Fast dynamic 30 MR spectroscopic imaging with compressed sensing and multiband excitation pulses for hyperpolarized 13C studies, Magnetic Resonance in Medicine, 2011, pp. 610-619.

* cited by examiner

METHOD FOR RECORDING MAGNETIC RESONANCE DATA, MAGNETIC RESONANCE FACILITY, COMPUTER PROGRAM AND ELECTRONICALLY READABLE DATA CARRIER

CROSS-REFERENCE TO RELATED APPLICATIONS

The present application claims the benefit of the filing date of German patent application no. 102019201385.6, filed on Feb. 4, 2019, the contents of which are incorporated herein by reference in their entirety.

TECHNICAL FIELD

The present disclosure relates to a method for recording magnetic resonance data.

BACKGROUND

Particularly in medical imaging, magnetic resonance imaging has proved to be an important and frequently used tool. Specifically in the field of medical technology, efforts are made to enable the fastest possible imaging, which simultaneously provides an excellent or at least adequate image quality. Echo-planar imaging (EPI) is regarded as one of the fastest methods for recording magnetic resonance data. Current medical imaging techniques using EPI have been inadequate.

SUMMARY

In a three-dimensional EPI magnetic resonance data recording procedure, following a single excitation period or "module," that is, within a so-called "shot", a plurality of k-space rows (and therefore a plurality of echoes) are recorded. The entire read-out period, in which the number of echoes (echo count) is recorded, is designated as an echo train. Herein referred to as 3D echo-planar imaging within an echo train, by means of the number of k-space rows, a particular proportion of the k-space that is designated a k-space partition is sampled. Therefore, the second phase encoding direction used in the three-dimensional magnetic resonance imaging is often referred to as the "partition direction".

In echo-planar imaging, it should be noted that the later-recorded k-space rows measure a smaller magnetic resonance signal than the earlier-recorded k-space rows. In order accordingly to obtain a useful magnetic resonance recording, it needs to be ensured that adjacent k-space rows in the k-space are recorded with as similar a signal decline as possible, since otherwise steps arise in the k-space that appear as artifacts (so-called "Gibbs ringing") in an image reconstructed from the magnetic resonance data. Therefore, it is preferable to keep the duration of the echo train smaller than or as long as the T2* relaxation time. Furthermore, it applies for the echo-planar imaging that the k-space is sampled faster in the read-out direction than in a phase encoding direction. As a result, image distortions can arise. In order to avoid this, the read-out speed is increased along the phase encoding direction, which can be achieved, for example, by means of acquisitions interleaved with one another or parallel imaging.

Another possibility for accelerating the imaging in magnetic resonance is the use of a so-called "compressed sensing" (CS). This involves an undersampling technology that uses special trajectories in the k-space to enable a randomized or pseudorandomized sampling pattern of the k-space. Through the use of such a randomization technology, convolution artifacts are "blurred" such that they act like image noise in the magnetic resonance images.

A combination of 3D-EPI with CS has so far not been enabled due to diverse contrary approaches. As discussed, it is necessary for compressed sensing to sample the k-space in a randomized manner, for which different randomization schemes are known, which lead to different sampling patterns. A known randomization scheme is the use of a Poisson disc for generating a variable density (the "variable density Poisson disc" technique). In concrete terms, the density of k-space rows that are intended to be sampled falls off radially and proceeding outwardly from the center of the k-space.

If a sampling pattern of this type were to sample radially or linearly outwardly from the inside or from left to right with an EPI echo train, severe image artifacts would arise. This is due to the fact that the size of the gradient pulses in the phase encoding direction, specifically the gradient strength, need to be varied to achieve a corresponding density variation, as occurs on use of a Poisson disc for generating variable density. This change in the gradient strength of the gradient pulses (often also called "phase-encoding blips") has the effect that spatial frequency-dependent distortions occur, which manifest with different strengths.

The reason for these distortions is that susceptibility differences can arise in the object to be recorded (e.g. a patient), and can lead to interfering gradient fields within the object to be recorded, the strength of which can lie within the order of magnitude of that of a weaker gradient pulse for changing the k-space row in EPI imaging. These gradient pulses of lower gradient strength in at least one of the phase encoding directions would occur in an application of compressed sensing to 3D EPI with Poisson disc sampling as a randomizing technique in the region of high density k-space rows to be sampled around the k-space center, that is, at low spatial frequencies. Ultimately, this would be reproduced in the magnetic resonance image resulting from the recorded magnetic resonance data through a resolution loss, since the low-frequency k-space regions are more severely distorted than the high-frequency k-space regions.

In the field of spectroscopy, it was proposed in an article by Benjamin J Geraghty et al. entitled "Accelerated 3D Echo-Planar Imaging with Compressed Sensing for Time-Resolved Hyperpolarized 13C Studies" in Magnetic Resonance in Medicine 77: 538-546 (2017) to apply random undersampling to the z-gradients in order to achieve a combination of 3D EPI and CS. But beyond this particular application case, it has mostly been proposed to use a combination with CAIPIRINHA for echo-planar imaging. Although this leads to shortened recording times, it has certain disadvantages in the actual implementation Thus, it is an object of the disclosure to provide a possibility for further shortening of the recording time in echo-planar imaging while maintaining good image quality. In order to achieve this, the embodiments as described herein include a method, a magnetic resonance facility, a computer program, and an electronically readable data carrier as discussed herein and according to the independent claims. Advantageous embodiments are further described in the dependent claims. As further discussed herein, a three-dimensional echo-planar imaging (EPI) sequence may be used, whereby following a single excitation period in an echo train, an echo count of k-space rows is read out in a read-out direction in the k-space, and interchanging takes place between these rows by means of gradient pulses of the two phase encoding directions.

In a method of the aforementioned type, according to an embodiment, it is also provided that for combination of the echo-planar imaging sequence with a compressed sensing technique:

a distribution of k-space rows to be sampled in the plane formed by the phase encoding directions, said distribution describing a spatially varying density, is determined according to a randomizing scheme of the compressed sensing technique;

the k-space to be sampled is partitioned into a subdivision count corresponding to the echo count, of in particular respectively coherent subspaces, wherein each subspace contains an equal number of k-space rows to be sampled according to the distribution;

for each echo train, a sequence of k-space rows to be sampled and each containing a k-space row from each subspace is determined such that the gradient pulses needed for the changeover between the k-space rows in the sequence for each phase encoding direction exceed a threshold value for the gradient strength; and recording magnetic resonance data with the sequences thus determined.

According to the present disclosure, therefore, a special sampling scheme is proposed to enable the use of a compressed sensing (CS) technique for 3D EPI recording processes. As described above, the greatest problem so far has been the variable density of the distribution of the k-space rows to be sampled, that is, the undersampling pattern. With conventional procedures, this would lead to the jumps in the k-space and thus the gradient pulses (phase encoding blips) used for changing becoming smaller for the (usually) low frequency subregions of the k-space with a greater density of k-space rows to be sampled than for regions of the k-space of lower density, usually subregions positioned further outwardly. This leads to, in regions of high density k-space rows to be sampled, more severe distortions occurring, while in both the others, weaker distortions occurring. This would result in artifacts, in particular, image smearing.

In contrast, the embodiments described in the present disclosure propose two measures to provide a sampling pattern that avoids such excessively small jumps in the k-space. Firstly, different regions in the k-space, specifically the subspaces, are defined, namely corresponding in quantity to the echo count, so that in each echo train, an echo can be recorded from each of these subspaces for which these subspaces suitably each contain an equal number of k-space rows to be sampled. This ensures that in each echo train, changing takes place at least between the individual subspaces. As a second measure, for changing between the k-space rows to be sampled in one echo train in the different subspaces, only those gradient pulses which require a minimum gradient strength are permitted. In other words, the strength of the phase encoding blip for both phase encoding directions should not fall below a respective threshold value. This threshold value can be selected, in particular, dependent upon the effective echo spacing, which may be selected to be not longer than, for example, 0.15 ms. This would typically correspond to undersampling with a factor of 8.

The sequences therefore correspond to different routes, that is, trajectories through the k-space to be sampled, whereby each subspace is visited once. The determination of such different sequences with phase encoding blips that are not too weak is achieved through a variation of the gradient strengths of the gradient pulses within the echo trains, which means that the individual phase encoding blips within an echo train are typically different.

Through the use of the threshold values, therefore, sufficiently large amplitudes of the gradient pulses are ensured so that together with the intelligent division (i.e. partitioning) of the k-space, the use of a density variation, even in the three-dimensional echo-planar imaging with very low smearing or, expressed more generally, artifacts, is enabled.

In this way, it is therefore possible to combine 3D EPI with CS, which leads to significantly shorter recording times in particular in comparison with a recording undersampled with CAIPIRINHA. The gradient strength of the gradient pulses lying between the individual echoes is hereby varied in both phase encoding directions, whereby in both phase encoding directions, threshold values ensure that "phase encoding blips," i.e. gradient pulses which are too weak in their gradient strength, are not used.

An echo count in any suitable range may be used, such as in a range of 5 to 20, for instance. Herein, the echo train is preferably kept short to be able to keep the echo count, and thus also the subdivision count (i.e. the number of subspaces) low, which itself provides, in principle, for large amplitudes of the gradient pulses, that is, high gradient strengths. In this regard, it is further suitable if, as often striven for in conventional techniques, the duration of the echo train that are selected to be shorter than a mean or smallest, in particular assumed and/or pre-determined, T2* relaxation time in the recording region. The use of short echo trains also contributes to the maintenance of this condition. This minimizes further possible image artifacts.

In concrete terms, the preparation of the actual recording process is thus initially intended, as is fundamental to compressed sensing techniques, to select a distribution of k-space rows to be recorded on the basis of the randomization scheme used. Thereby, a Poisson disc sampling is used in a particularly advantageous manner as a randomization scheme, and therefore the aforementioned "variable density Poisson disc" approach may be selected. Such a randomization scheme typically leads to a distribution in which a very high density of k-space rows to be sampled is present in the k-space center, which decreases radially outwardly to an ever greater extent. In this regard, it is furthermore also particularly advantageous if an at least substantially circular or elliptical k-space to be sampled is used in the plane of the phase encoding directions.

Once the distribution of the k-space rows to be sampled in the plane formed by the phase encoding directions, in which therefore each point corresponds to a k-space row is determined, a subdivision of the k-space to be sampled into a subdivision count of subspaces that is equal to the echo count is undertaken such that in each subspace, an equal number of k-space rows to be sampled is contained according to the distribution. Herein, the subspaces may be coherent. Furthermore, in this regard the sequence of a fixed succession of adjacent subspaces may be correspondingly selected. This may be particularly advantageous to assist in achieving a comparable signal decline between adjacent sampled k-space rows. This is because only a single excitation period is used for each echo train, and thus the magnetic resonance signal declines with time so that in later echoes a weaker magnetic resonance signal is measured. If a pre-determined succession of subspaces is maintained for each echo train, the echoes of each subspace are measured at the same time point within the echo train. If the sequential subspaces in the succession are also spatially adjacent, a minimal signal decline also occurs between such adjacent subspaces so that a larger step, which could lead to artifacts, is avoided. Thus, if through the partitioning of the k-space into the subspaces, a direction is enabled which permits a successive stepping through the defined subspaces and thus at each site, the smallest possible "steps" at the limits of the subspaces.

In an exemplary embodiment of the present disclosure, it can be provided in this context that the partitioning of the k-space to be sampled takes place at least partially along at least one of the phase encoding directions. If the phase encoding directions in the k-space thus correspond to the ky-direction and the kz-direction, then the successive subspaces in one of the phase encoding directions can be separated by separation lines extending in the other phase encoding direction. For example, the subspaces can then follow one another in the ky-direction. In cases in which a particularly high density of k-space lines is present in the k-space center, this typically leads to the width of the subspaces decreasing toward the k-space center, and then increasing again.

However, in another embodiment of the present disclosure, it can also be provided that the partitioning of the k-space to be sampled takes place at least partially in the radial direction. For instance, if an even density decrease takes place in the radial direction, such a process can be suitable. For example, the sampling can take place from the outermost subspace to the innermost subspace containing the k-space center, or vice versa, such as when a predetermined succession of adjacent subspaces is to be used.

Also conceivable, however, is an at least partial combination of these two possibilities for defining the subspaces. In an advantageous embodiment, for example, it can be provided that a circular or elliptical region around the k-space center forms a first subspace, while an annular ring or elliptical ring adjacent thereto is divided by a separation line, for instance a separation line extending along one of the phase encoding directions, into a second and a third subspace. The same can then be achieved for circular rings or regions of the k-space lying further out so that, for example, given an echo count of five in the aforementioned example, two further subspaces arise, specifically a fourth and a fifth subspace. Then, the fixed succession could, for example, provide that initially a k-space row in the fifth subspace is sampled, then a k-space row in the adjacent second subspace, then a k-space row in the central first subspace, then a k-space row in the third subspace adjacent thereto on the other side and, finally, a k-space row in the fourth subspace adjacent thereto.

Since a plurality of k-space rows to be sampled is usually contained in each of the defined subspaces, it is the object of the subsequent step to determine sequences of k-space lines to be sampled for different echo trains, such that the gradient pulses needed for the change between the k-space rows in a sequence, i.e. the phase encoding blips, exceed for each phase encoding direction a threshold value for the gradient strength, in particular, therefore a threshold value in relation to its amplitude. If, in fact, the threshold values and the echo count have once been selected such that this permits no determination of sequences that fulfill these conditions, for example because subspaces must be defined too small, then for example the echo count, that is, the number of k-space rows to be sampled per sequence/excitation period, can be reduced.

Once all the sequences have been determined, the recording of the magnetic resonance data can take place making use of these sequences. This means that in each repetition of excitation period and echo train, one of the subsequent k-space rows is measured with corresponding varying gradient pulses for changing between these.

As mentioned above, the use of the threshold value corresponding to a minimum gradient strength serves for avoiding the occurrence of excessively strong distortions, for example in conjunction with interfering gradient fields which can arise due to susceptibility differences. Accordingly, a particularly advantageous embodiment of the present disclosure provides that the threshold values are selected such that the gradient strength of the gradient pulses of the sequence amounts to any suitable multiple (e.g. at least double, three times, five times, etc.) the gradient strength of interfering gradient fields occurring due to susceptibility differences in the object to be recorded. These interfering gradient fields and thus the threshold values, if no calculation possibility is available by analytical calculation and/or by simulation, can therefore be determined substantially by means of empirical values. It is however also possible to determine the threshold values additionally or alternatively in at least one calibration measurement in an artifact-minimizing manner, for instance. Hereby, for example, a phantom can be used which can also contain, for instance, susceptibility differences as are present in a patient as the object to be investigated. In principle, but less preferably due to the prolongation of the examination duration, it is also conceivable to carry out the calibration scan on the object to be recorded.

Suitably, the threshold values can be selected dependent upon at least one recording parameter describing, for example, the object to be recorded and/or the recording target. For different objects to be recorded, for example different recording regions of a patient, different susceptibility differences can occur. This can be taken into account accordingly upon selection of the threshold value. Furthermore, different recording techniques, which are selected dependent upon the recording target, can also lead to a different relevance of distortions so that dependent upon the recording target, different threshold values are also put to use.

In a development of the disclosure, it can be provided that for at least one of the phase encoding directions, an upper limit value is also used for the gradient strength that is chosen to be greater than the corresponding threshold value. In this way, for example, an increase in the measurement time or the echo spacings due to excessively large spacings to be covered in the k-space can be avoided; furthermore, system-inherent limitations of the magnetic resonance facility can also be taken into account herein.

It should also be noted at this point that the recording technique described herein can be used for the combination of 3D EPI and CS to different application cases, such as recording goals, for instance. For example, by means of the method embodiments as described herein, anatomical T2*-weighted imaging, functional imaging, diffusion-weighted imaging, and/or perfusion-weighted imaging can be realized. All these applications are significantly accelerated by means of the present disclosure. This enables significantly shorter scan times and/or higher resolution imaging within clinically acceptable scan times.

It should further be noted at this point that, in principle, variants of the present disclosure are also conceivable in which in a sequence, and thus in an echo train, a plurality of k-space rows of a subspace to be read out are read out directly after one another, for example, when using a GRASE technique. Then, for example, a gradient echo and a spin echo can be measured successively within a subspace.

Alongside the method, the present disclosure also relates to a magnetic resonance facility comprising a control facility configured for carrying out the method according to the disclosure. All the embodiments relating to the method embodiments can be transferred similarly to the magnetic resonance facility embodiments, so that the aforementioned advantages can therefore also be achieved therewith.

The control facility can comprise at least one processor and at least one storage means. In particular, in addition to a sequence control facility which also controls the recording of the magnetic resonance data, the control facility can comprise a distribution determining unit for determining the distribution of k-space rows to be sampled according to the randomization scheme, a partitioning unit for partitioning the k-space to be sampled into subspaces, and a sequence determining unit for determining the corresponding sequences for each echo train. Further functional units or subunits for realizing steps of preferred embodiments are naturally also conceivable.

In an embodiment, a computer program may be, for example, directly loadable into a memory store of a control facility of a magnetic resonance facility and has program means to carry out the steps of one or more of the method embodiments when the computer program is executed in the control facility of the magnetic resonance facility.

The computer program can be stored on any suitable type of storage media, such as a non-transitory computer-readable medium that is implemented as an electronically readable data carrier, which therefore comprises electronically-readable control information stored thereon, and which comprises at least one computer program embodiment as discussed herein and is configured such that, on use of the data carrier in a control facility of a magnetic resonance facility, said control information carries out one or more of the method embodiments. The data carrier can be, for example, a hard disk, a CD-ROM, volatile or non-volatile memory, etc.

BRIEF DESCRIPTION OF THE DRAWINGS/FIGURES

Further advantages and details of the present disclosure are further explained in the exemplary embodiments described below and by reference to the drawings, in which.

DETAILED DESCRIPTION

Figure 1:
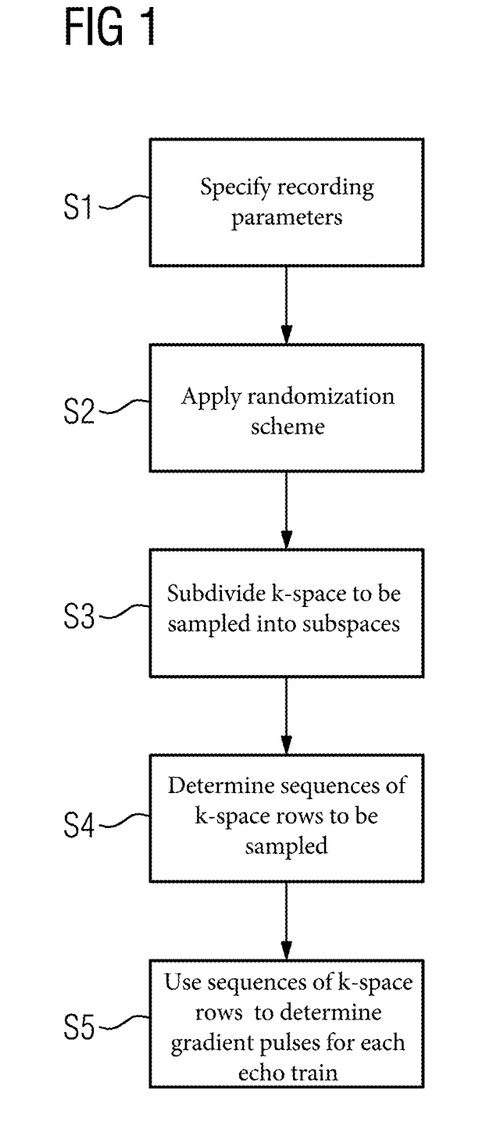
FIG. 1 shows a flow diagram of an example method, in accordance with an embodiment of the present disclosure.

FIG. 1 shows a flow diagram of an example method, in accordance with an embodiment of the present disclosure. Thereby, in the present case, magnetic resonance data from a recording region of a patient as the object to be investigated is recorded, wherein different recording goals and thus overall protocols are conceivable, for example, anatomical T2*-weighted imaging, functional imaging, diffusion-weighted imaging and/or perfusion-weighted imaging. What is central herein is that the protocols used for the recording use a three-dimensional echo-planar imaging sequence (3D EPI sequence). The necessary basic settings for the recording parameters are undertaken in a step S1. In particular, hereby a user selects to achieve an acceleration of the imaging (or an improvement in the image quality with the same duration of the imaging) in that compressed sensing (CS) is used in combination with the 3D EPI sequence.

Recording parameters that are specified in step S1 also comprising, in particular, in the present case the echo count, that is, how many echoes are to be recorded in the echo train after the excitation period. Furthermore, for the compressed sensing technique, a randomization scheme is specified, for example, a Poisson disc sampling. Similarly, as early as in S1, a determination can take place of threshold values which are to exceed the gradient strength of the still to be determined gradient pulses in the phase encoding directions, by means of which a changeover between the k-space rows to be sampled as individual echoes is to take place. These threshold values can be selected, for example, dependent upon the recording region and/or the recording goal and have been pre-determined in the present case.

The pre-determination has taken place such that the gradient strength of the gradient pulses of the sequence amounts to at least double, three time, five times, etc., the gradient strength of interfering gradient fields occurring, for instance, due to susceptibility differences in the object to be recorded, in this case the patient. If the gradient strength of the gradient pulses, in particular defined by their amplitude, lies in the region of the gradient strength of such interfering gradient fields which can arise, for example, through boundary surfaces of air and tissue within the patient, then clearly visible distortions occur which are visible as artifacts in a magnetic resonance image derived from the magnetic resonance data.

The determination in such a manner that such distortions due to the variable density distribution of k-space rows to be sampled would be sequence-dependent in the case of compressed sensing, as far as possible do not occur is hereby fundamentally analytically conceivable, for example, in the context of an estimation of the interference gradient fields, but it is preferable to undertake the pre-determination of the threshold values empirically and/or in the context of a calibration scan. Accordingly, particular threshold values for recording parameters, dependent upon which many can be selected, can then be stored in a database of a control facility of the magnetic resonance facility or other suitable storage location, so that they are retrievable in step S1.

Together with the threshold values which form a lower limit for the gradient strength for avoiding too severely frequency-dependent distortions, for each of the phase encoding directions, as early as step S1, limit values can be selected which can define an upper limit for the gradient strength.

In a step S2, the randomization scheme is applied to determine, in the k-space to be sampled, the position, in the read out direction, of k-space rows to be sampled, herein for example, the kx-direction. In the two phase encoding directions, here the ky-direction and the kz-direction, that is, the plane formed by these phase encoding directions, the position of k-space rows to be sampled, is therefore identified by points.

Figure 2:
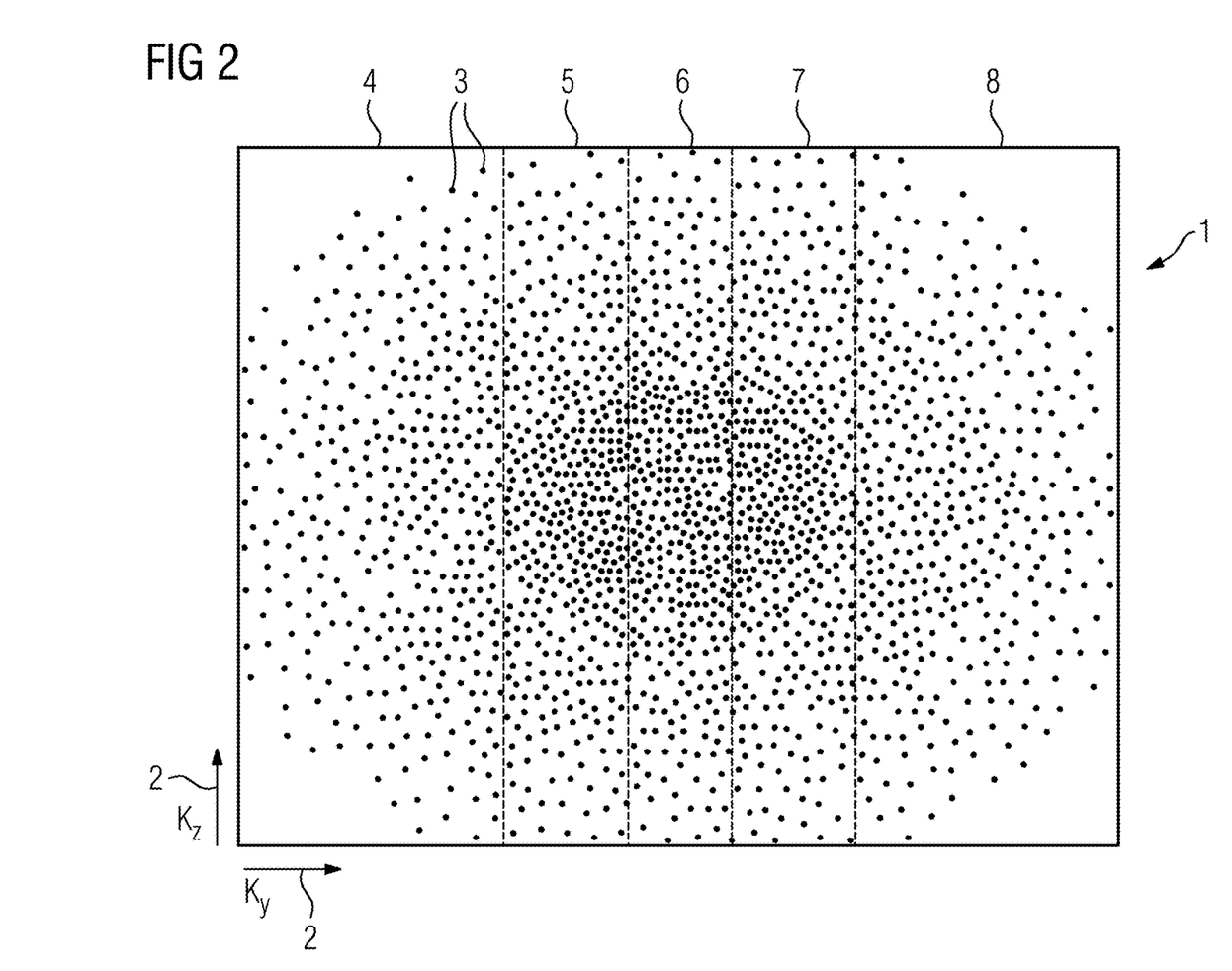
FIG. 2 shows a first example for partitioning of the k-space to be sampled, in accordance with an embodiment of the present disclosure.

FIG. 2 shows an exemplary embodiment in which a Poisson disc sampling has been used as a randomization scheme for generating a variable density of k-space rows. The points 3 recognizable in the k-space 1, wherein the phase encoding directions kz and ky are identified by arrows 2, therefore each denote a k-space row to be sampled. As can be seen, the density of k-space rows to be sampled decreases, starting from the k-space center outwardly, as is characteristic of a Poisson disc sampling. In this case, as can be seen from the lack of points 3 in the corners, the k-space 1 to be sampled is selected to be substantially elliptical.

In a step S3 (see FIG. 1), the k-space 1 to be sampled is subdivided into different subspaces, the number of which corresponds to the echo count. In the present exemplary embodiment, to enable a simple representation, an echo count of five has been selected, although excellent results have also been achieved at higher echo counts, for example up to an echo count of 20, wherein in practice, for example, an echo count of nine shows good results.

The partitioning of the k-space 1 into subspaces takes place in that, in each of the subspaces formed, there is an equal number of k-space rows to be sampled, thus according to FIG. 2, the points 3. For the echo count of 5 and a division along the ky-direction, according to FIG. 2, the subspaces 4, 5, 6, 7, 8 are formed. Thereby, the subspace 6 that contains the k-space center has the smallest width in the ky-direction, since there the density of k-space rows (and therefore points 3 according to FIG. 2) to be sampled is the greatest.

On the basis of this division, in a step S4 (see FIG. 1), sequences of k-space rows to be sampled, thus according to FIG. 2, the points 3 are determined, wherein in the present case a fixed pre-determined sequence of the subspaces 4 to 8 is utilized. The fixed pre-determined sequence of the subspaces 4 to 8 is, in the present case, have an order in the positive ky-direction so that the read-out sequence is subspace 4, subspace 5, subspace 6, subspace 7, subspace 8. According to each sequence to be determined, which relates to an echo train, according to the sequence exactly one k-space row is sampled for each of the subspaces 4 to 8. Since the sequence is pre-determined and the signal strength diminishes over the length of the echo train, that is with each echo, for each of the subspaces 4 to 8 a signal strength of the magnetic resonance signal is present, which remains constant, whereby due to the firmly pre-determined sequence, and thus the order of adjacent subspaces 4 to 8, only weak steps occur between the individual pairs of subspaces 4 to 8. Overall, therefore, the signal decline between adjacent k-space rows is limited in each case.

In order to determine the sequences, a k-space row, identified by points 3 in FIG. 2 that is to be sampled in each case is thus extracted, wherein as an additional condition for the k-space rows of a sequence, it is however also required that they have a certain spacing along both phase encoding directions, which is expressed in the condition that the gradient strengths of the gradient pulses of the phase encoding directions that are necessary for the change to the next k-space row of the sequence to be sampled and are also designated phase encoding blips exceed the respective threshold value for both phase encoding directions.

Figure 3:
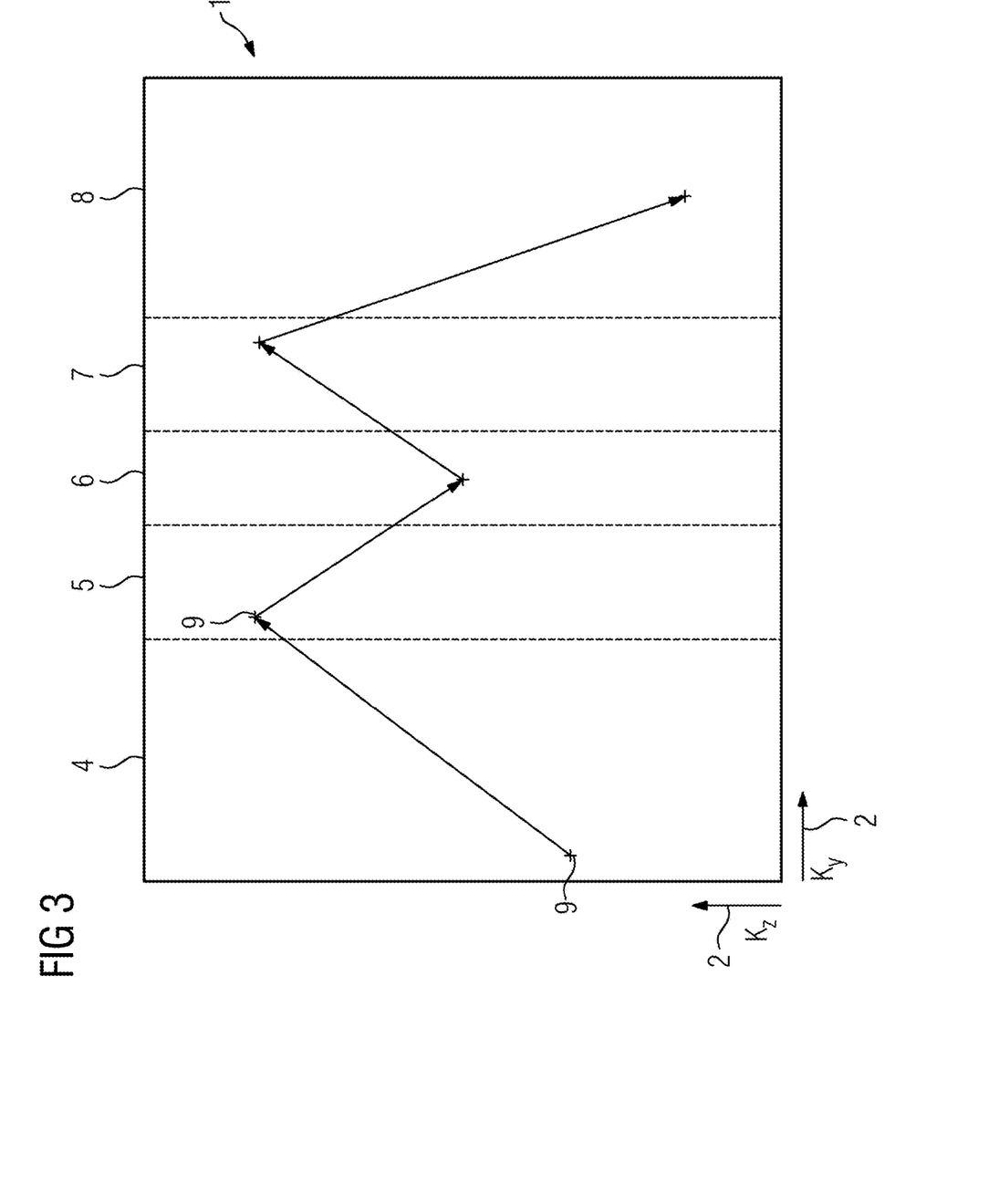
FIG. 3 shows an example sequence of k-space rows to be sampled, in accordance with an embodiment of the present disclosure.

An exemplary sequence of k-space rows to be sampled and marked by points 9 is shown in FIG. 3. Each of the points 9 clearly lies in a different one of the subspaces 4 to 8. It should be noted that overall a number of sequences results, which corresponds to the number of the k-space rows in each subspace 4 to 8, once each of the k-space rows selected according to the randomization scheme and to be sampled is naturally only measured once.

Figure 4:
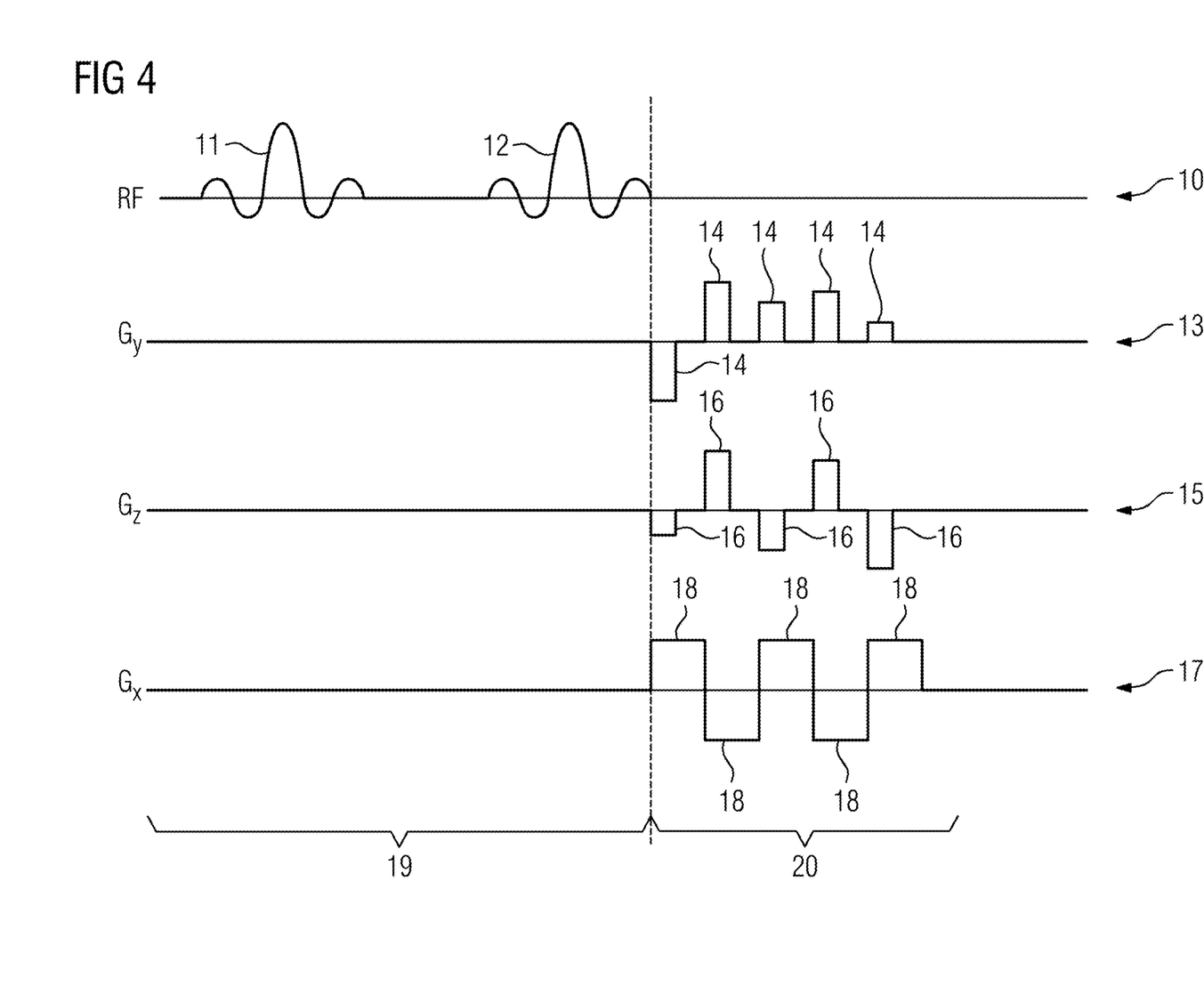
FIG. 4 shows an example schematic sequence diagram for the sampling according to FIG. 3, in accordance with an embodiment of the present disclosure.

FIG. 4 shows by way of example, the implementation in a simplified sequence diagram. In the first line 10, high frequency pulses 11, 12 are indicated, in the second line 13, output gradient pulses 14 (phase encoding blips) of the first phase encoding direction for selecting a k-space row to be sampled are shown, in the third line 15, corresponding gradient pulses 16 of the second phase encoding direction (partition direction) and in the fourth line 17, read-out gradient pulses 18.

In the present case, by way of example, in the excitation period 19, two high frequency pulses 11 and 12 are used, wherein the high frequency pulse 11 is a 90° excitation pulse, the high frequency pulse 12 is a 180° inversion pulse. Naturally, other embodiments are also conceivable.

In the echo train 20, by means of respective read-out gradient pulses 18, the five echoes are read out. Clearly visible is the variation of the gradient strength of the gradient pulses 14 and 16, although all exceed the respective threshold value for the corresponding phase encoding direction.

If it is ascertained in step S4 that no complete set of sequences of k-space rows to be sampled exists in which for each sequence the threshold values (and if relevant, the limit values) are adhered to, this can be due, for example, to an excessively high echo count which requires excessively small subspaces 4 to 8. Then a change can be demanded by a user, for example, a reduction in the echo count.

In a step S5 (see FIG. 1), the determined sequences are then used to specifically determine and to output corresponding gradient pulses 14, 16 for each echo train, as shown in FIG. 4, which means that the magnetic resonance data is measured using the sequences as recorded in step S4. The magnetic resonance data record arising can then be further processed, as known, for example, for generating a magnetic resonance image to be displayed and/or stored.

Figure 5:
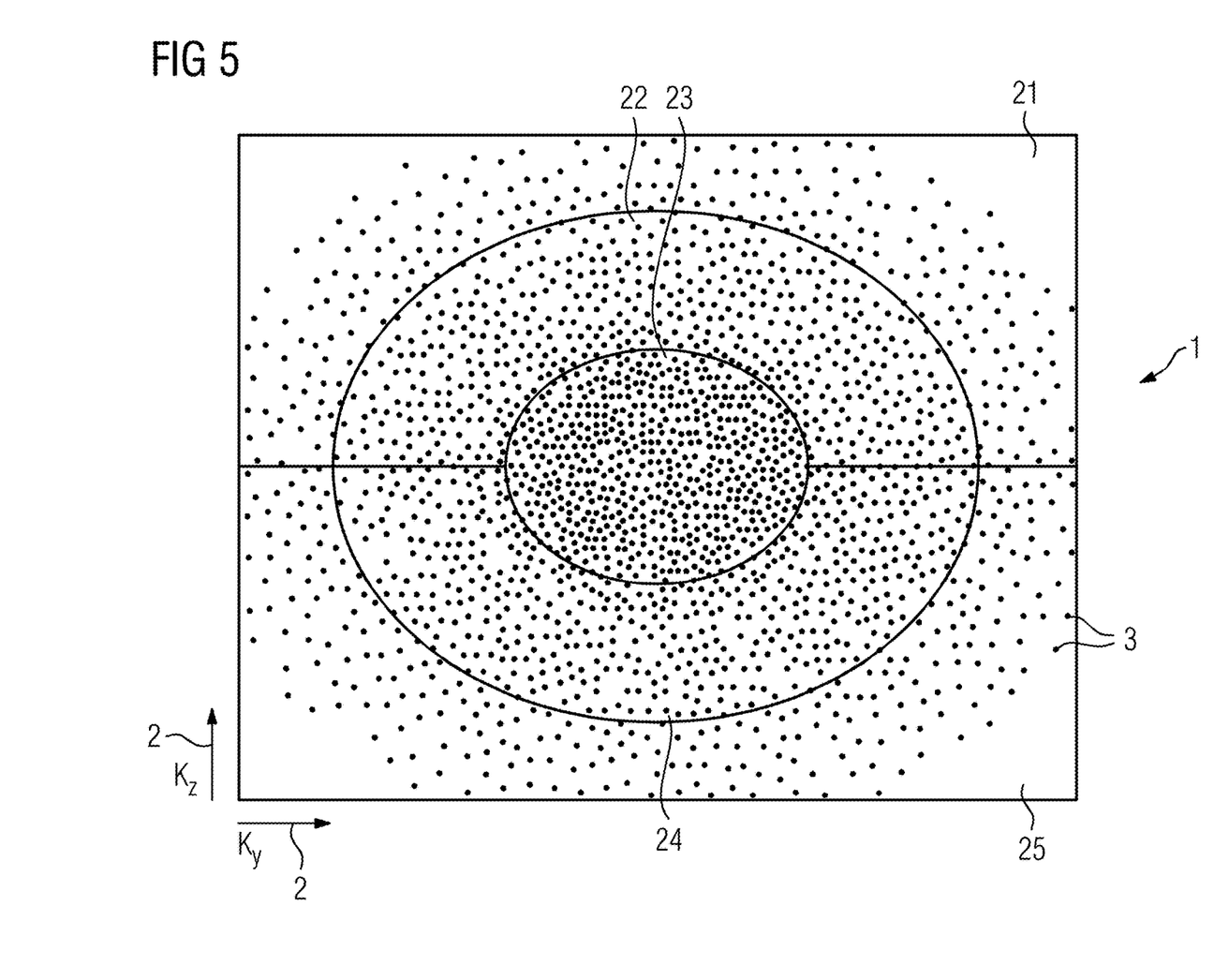
FIG. 5 shows a second example for partitioning of the k-space to be sampled, in accordance with an embodiment of the present disclosure.
Figure 6:
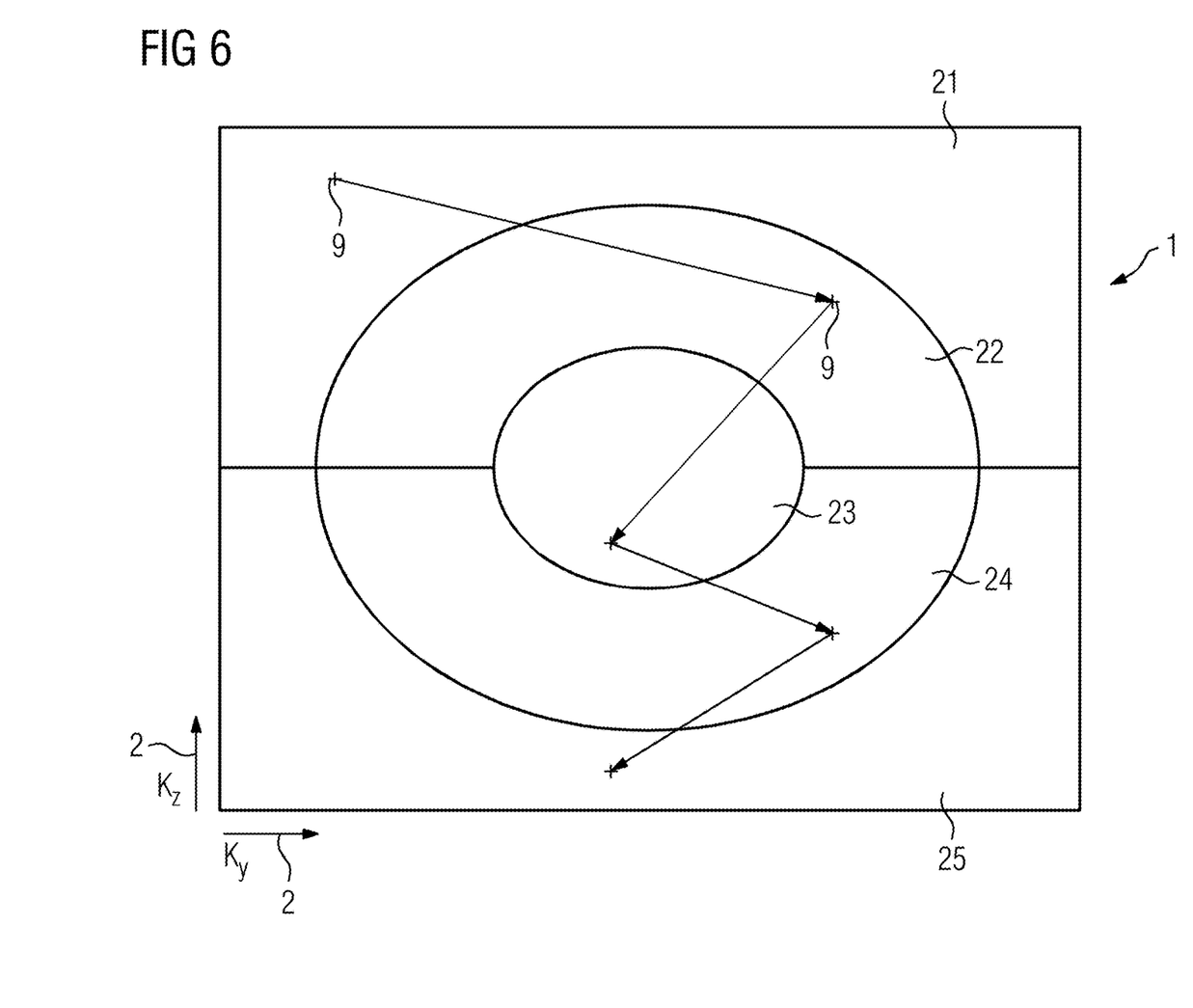
FIG. 6 shows an example sequence of k-space rows to be sampled with the division according to FIG. 5, in accordance with an embodiment of the present disclosure.

FIGS. 5 and 6 indicate an alternative possibility for partitioning the k-space 1 to be sampled 1 into subspaces 21 to 25, wherein in the present case, a radial partitioning has been at least partially undertaken. The pre-determined sequence of the subspaces is, in this example, subspace 21, subspace 22, subspace 23, subspace 24 and subspace 25, so that initially in the upper region, progress is from radially outwardly to the k-space center (subspace 23), whereupon in the lower region, it moves radially outwardly again therefrom. In a pre-determined sequence of this type, although somewhat stronger steps in the signal strength occur, in particular, between the subspaces 21 and 25, due to the less divided boundary and due to the low density of k-space rows to be sampled, this has proved to be less critical.

A corresponding possible sequence of k-space rows to be sampled and marked anew by points 9 is shown in FIG. 6.

It should be noted that, in particular, for relatively large echo counts, it is also conceivable to undertake an exclusively radial partitioning of the k-space 1 to be sampled.

Figure 7:
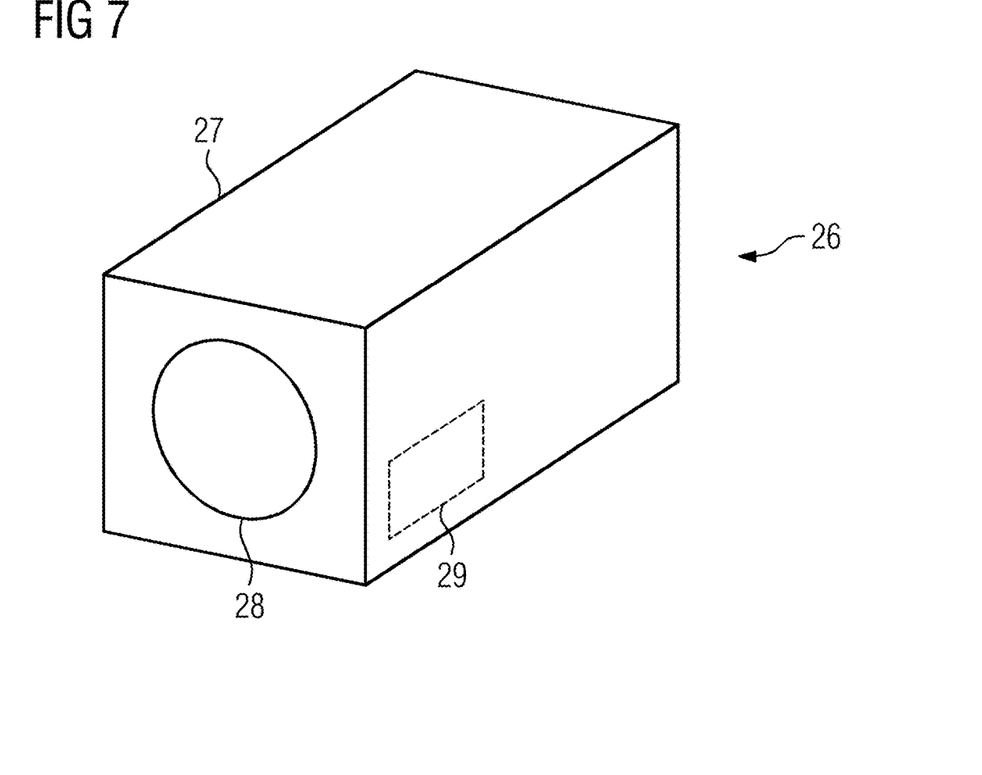
FIG. 7 shows an example magnetic resonance facility, in accordance with an embodiment of the present disclosure.

FIG. 7 shows a sketch of the principle of a magnetic resonance facility 26 (e.g. a magnetic resonance imager or magnetic resonance imaging system) according to the disclosure. This comprises, as known in principle, a main magnet unit 27 (e.g. a magnetic data acquisition unit or scanner) that defines a patient receiving space 28 into which a patient can be moved by means of a patient support (not shown in further detail here). Surrounding the patient support, a high frequency arrangement of the magnetic resonance facility 26 and a gradient coil arrangement of the magnetic resonance facility 26 can be provided and, for the sake of clarity, these are also not shown.

The operation of the magnetic resonance facility 26 is controlled by a control facility 29, which is also configured for carrying out the method embodiments as described herein. The control facility may be implemented, for example, as one or more computer processors. Thus, the various components of the control facility 29 as discussed below may be implemented as separate processors, or their respective functions shared among one or more processors of the control facility 29. The various functions of the components of the control facility 29, which are discussed directly below, may be achieved via any suitable combination of one or more hardware processors, software, or a combination of both.

Figure 8:
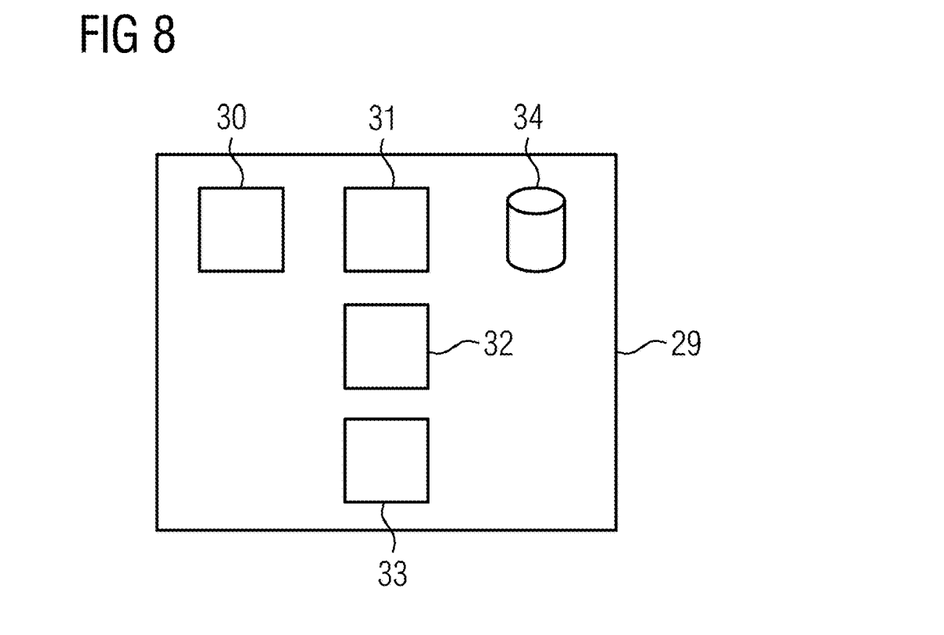
FIG. 8 shows the functional structure of an example control facility of the magnetic resonance facility according to FIG. 7, in accordance with an embodiment of the present disclosure.

FIG. 8 shows in more detail the functional structure of the control facility 29. According to this, the control facility 29 comprises, as known in principle, a sequence unit 30 by means of which the recording of magnetic resonance data (see S5 in FIG. 1) takes place. For the performance of the method embodiments as described herein, the control facility 29 further comprises a distribution determining unit 31 for carrying out the step S2, a partitioning unit 32 for carrying out the step S3, and a sequence determining unit 33 for carrying out the step S4. Optionally, a database 34 can also be stored in a corresponding storage means in the control facility 29 or at another suitable accessible location, from which threshold values and also, if relevant, limit values, can be retrieved.

Figure 9:
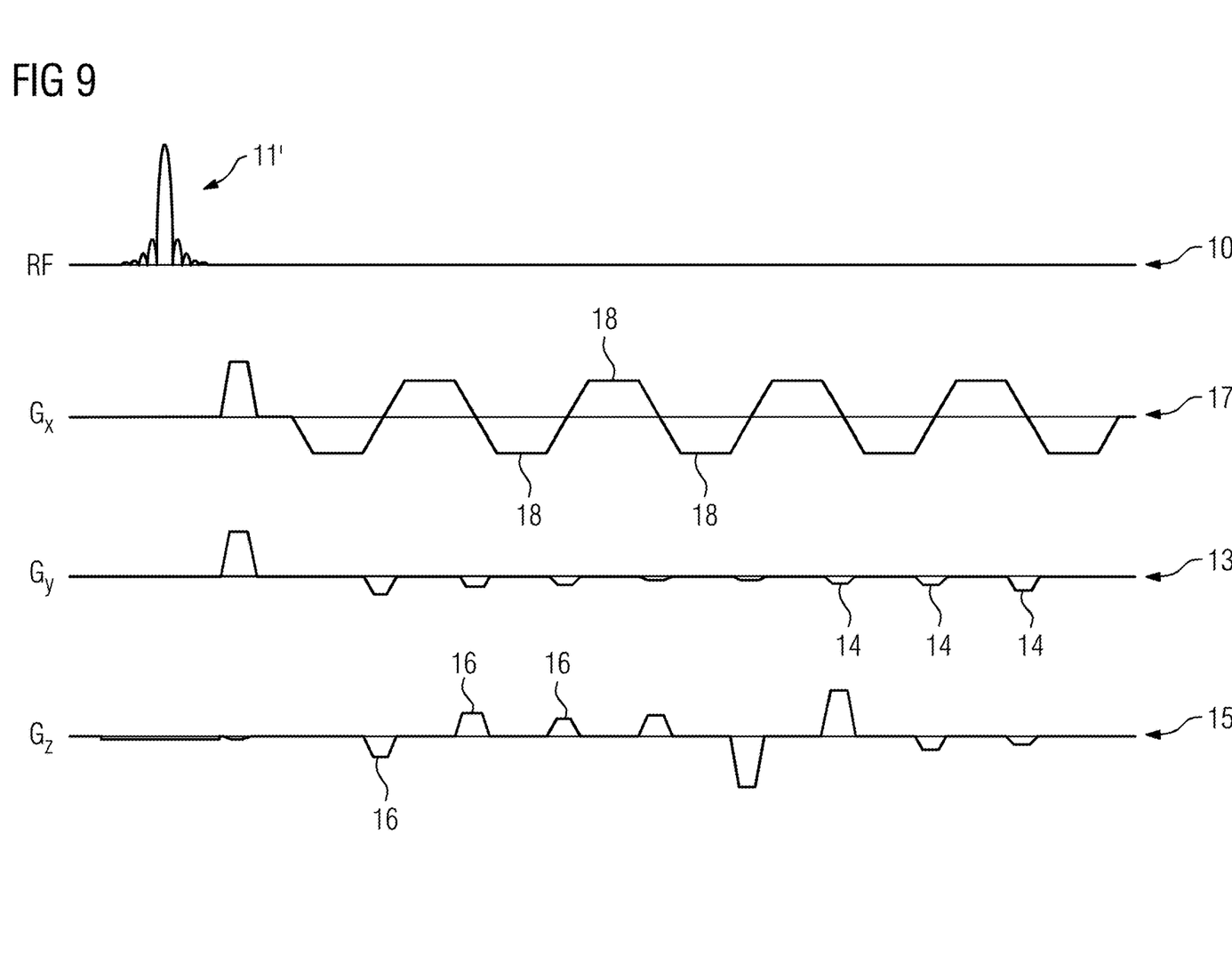
FIG. 9 shows an example sequence diagram for the application of the method, in accordance with an embodiment of the present disclosure.

Finally, FIG. 9 shows a detailed example of a sequence diagram for use in accordance with the method embodiments as described herein, whereby in this case, in the line 10 (RF), only one high frequency pulse 11' is shown. The gradient pulses 14, 16 and 18 of lines 13, 15 and 16 are shown in this case with their corresponding flanks. Read-out always takes place, as known in principle, along the constant portions of the read-out gradient pulses 18. As also clearly shown in FIG. 9, the strengths of the gradient pulses 14, 16 are varied in order to realize a sequence of k-space rows to be sampled in the different subspaces, in this case, nine subspaces.

Although the disclosure has been illustrated and described in detail with the preferred exemplary embodiments, the disclosure is not restricted by the examples disclosed herein, and other variations can be derived therefrom by a person skilled in the art without departing from the protective scope of the disclosure.

What is claimed is:

1. A method for recording, with a magnetic resonance imager, magnetic resonance data of an object using a three-dimensional echo-planar imaging sequence, the method comprising:

reading out, following a single excitation period for an echo train, an echo count of k-space rows in a read-out direction in the k-space by interchanging between k-space rows by means of gradient pulses of two phase encoding directions;

determining a distribution of k-space rows to be sampled from a plane formed by the two phase encoding directions, the distribution of k-space rows describing a spatially-varying density and being determined according to a randomizing scheme of a compressed sensing technique;

partitioning the k-space rows to be sampled into a subdivision count corresponding to an echo count of respectively coherent subspaces, each one of the coherent subspaces containing an equal number of k-space rows to be sampled according to the distribution of k-space rows;

determining, for the echo train, a sequence of k-space rows to be sampled, each sequence containing a k-space row from each coherent subspace such that the gradient pulses needed for the interchange between the k-space rows in the sequence for each phase encoding direction exceed a respective threshold gradient strength value, and recording magnetic resonance data using the determined sequence of k-space rows for the echo train.

2. The method as claimed in claim 1, wherein the threshold gradient strength values are determined using at least one of (i) selected such that a gradient strength of the gradient pulses of each sequence of k-space rows to be sampled is equal to at least double a gradient strength and up to five times the gradient strength of interfering gradient fields that occur due to susceptibility differences in the object to be recorded, (ii) determined empirically, and/or (iii) determined in at least one calibration measurement, selected in an artifact minimizing manner.

3. The method as claimed in claim 1, wherein the threshold gradient strength values are selected dependent upon at least one recording parameter describing at least one of (i) the object, and (ii) a recording goal.

4. The method as claimed in claim 1, wherein, for at least one of the two phase encoding directions, an upper limit value is used as the threshold gradient strength value that is greater than the corresponding threshold gradient strength value.

5. The method as claimed in claim 1, wherein the randomization scheme includes at least one of (i) a Poisson disc sampling, and (ii) sampling of a k-space that is substantially circular or elliptical in the plane formed by the two phase encoding directions.

6. The method as claimed in claim 1, wherein the distribution of the k-space rows to be sampled is performed at least partially along at least one of the two phase encoding directions.

7. The method as claimed in claim 1, wherein the distribution of the k-space rows to be sampled is performed at least partially in a radial direction.

8. The method as claimed in claim 1, wherein a duration of the echo train is selected to be shorter than (i) a mean pre-determined T2* relaxation time, or (ii) a smallest pre-determined T2* relaxation time, in the recording region associated with the object.

9. The method as claimed in claim 1, wherein the sequence of k-space rows to be sampled are determined such that the sequences have at least one of (i) a fixed succession of adjacent subspaces, and (ii) an echo count in a range between 5 and 20.

10. A magnetic resonance imager for recording magnetic resonance data of an object using a three-dimensional echo-planar imaging sequence, the magnetic resonance imager comprising:

a memory configured to store computer-readable instructions; and a control facility configured to execute the computer-readable instructions stored on the memory to:

read out, following a single excitation period for an echo train, an echo count of k-space rows in a read-out direction in the k-space by interchanging between k-space rows by means of gradient pulses of two phase encoding directions;

determine a distribution of k-space rows to be sampled from a plane formed by the two phase encoding directions, the distribution of k-space rows describing a spatially-varying density and being determined according to a randomizing scheme of a compressed sensing technique;

partition the k-space rows to be sampled into a subdivision count corresponding to an echo count of respectively coherent subspaces, each one of the coherent subspaces containing an equal number of k-space rows to be sampled according to the distribution of k-space rows;

determine, for the echo train, a sequence of k-space rows to be sampled, each sequence containing a k-space row from each coherent subspace such that the gradient pulses needed for the interchange between the k-space rows in the sequence for each phase encoding direction exceed a respective threshold gradient strength value, and record magnetic resonance data using the determined sequence of k-space rows for the echo train.

11. A non-transitory computer-readable medium having instructions stored thereon that, when executed by one or more processors of a magnetic resonance imager, cause the magnetic resonance imager to record magnetic resonance data of an object using a three-dimensional echo-planar imaging sequence by:

reading out, following a single excitation period for an echo train, an echo count of k-space rows in a read-out direction in the k-space by interchanging between k-space rows by means of gradient pulses of two phase encoding directions;

determining a distribution of k-space rows to be sampled from a plane formed by the two phase encoding directions, the distribution of k-space rows describing a spatially-varying density and being determined according to a randomizing scheme of a compressed sensing technique;

partitioning the k-space rows to be sampled into a subdivision count corresponding to an echo count of respectively coherent subspaces, each one of the coherent subspaces containing an equal number of k-space rows to be sampled according to the distribution of k-space rows;

determining, for the echo train, a sequence of k-space rows to be sampled, each sequence containing a k-space row from each coherent subspace such that the gradient pulses needed for the interchange between the k-space rows in the sequence for each phase encoding direction exceed a respective threshold gradient strength value, and recording magnetic resonance data using the determined sequence of k-space rows for the echo train.

* * * * *